(12) United States Patent
Tanigami et al.

(10) Patent No.: US 10,682,155 B2
(45) Date of Patent: Jun. 16, 2020

(54) ULTRASONIC TREATMENT SYSTEM FOR JOINT

(71) Applicant: OLYMPUS CORPORATION, Hachioji-shi, Tokyo (JP)

(72) Inventors: Yasuo Tanigami, Hachioji (JP); Ryo Miyasaka, Hachioji (JP); Koji Kimoto, Tachikawa (JP); Hiroto Nakamura, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 105 days.

(21) Appl. No.: 16/146,060

(22) Filed: Sep. 28, 2018

(65) Prior Publication Data

US 2019/0029709 A1    Jan. 31, 2019

Related U.S. Application Data

(63) Continuation of application No. PCT/JP2016/060780, filed on Mar. 31, 2016.

(51) Int. Cl.
*A61B 17/16* (2006.01)
*A61B 17/32* (2006.01)

(52) U.S. Cl.
CPC ...... *A61B 17/320068* (2013.01); *A61B 17/16* (2013.01); *A61B 17/1626* (2013.01);
(Continued)

(58) Field of Classification Search
CPC . A61B 17/16; A61B 17/1622; A61B 17/1624; A61B 17/1628; A61B 17/1659;
(Continued)

(56) References Cited

U.S. PATENT DOCUMENTS 4,827,911 A * 5/1989 Broadwin ........ A61B 17/22012
310/17
6,068,628 A * 5/2000 Fanton ........... A61B 17/320016
606/28
(Continued)

FOREIGN PATENT DOCUMENTS

JP   2003-116870 A   4/2003
JP   2015-520620 A   7/2015
WO   2015/021216 A1  2/2015

OTHER PUBLICATIONS

Jun. 14, 2016 International Search Report issued in International Patent Application No. PCT/JP2016/060780.
(Continued)

*Primary Examiner* — Eric S Gibson
(74) *Attorney, Agent, or Firm* — Oliff PLC

(57) ABSTRACT

An ultrasonic treatment system for a joint has an ultrasonic transducer configured to generate ultrasonic vibration at a predetermined frequency, a treatment unit configured to treat a bone or a cartilage with the ultrasonic vibration, a frequency measurement unit configured to measure the frequency of the ultrasonic vibration of the treatment unit, a calculation unit configured to calculate a tilt indicating change, in a predetermined time, of the frequency measured with the frequency measurement unit, and a controller configured to determine whether change of absolute value of the tilt is equal to or larger than predetermined absolute value of the tilt.

6 Claims, 6 Drawing Sheets

(52) U.S. Cl.
CPC ............. *A61B 17/1659* (2013.01); *A61B 2017/320082* (2017.08)

(58) Field of Classification Search
CPC . A61B 17/1662; A61B 17/1675; A61B 17/32; A61B 17/320068; A61B 17/320069; A61B 17/320072; A61B 17/320074; A61B 17/320075; A61B 17/320077
See application file for complete search history.

(56) References Cited

U.S. PATENT DOCUMENTS

| | | | | |
|---|---|---|---|---|
| 6,379,371 | B1* | 4/2002 | Novak | A61B 17/320068 606/169 |
| 6,443,969 | B1* | 9/2002 | Novak | A61B 17/320068 606/169 |
| 6,544,260 | B1* | 4/2003 | Markel | A61B 17/320016 606/41 |
| 6,671,535 | B1* | 12/2003 | McNichols | A61B 5/0008 600/407 |
| 9,782,218 | B2* | 10/2017 | Konishi | A61B 18/1445 |
| 9,788,852 | B2* | 10/2017 | Voic | A61B 17/14 |
| 2003/0073987 | A1* | 4/2003 | Sakurai | A61B 18/08 606/28 |
| 2006/0047331 | A1* | 3/2006 | Lax | A61B 18/148 607/99 |
| 2008/0009848 | A1* | 1/2008 | Paraschiv | A61B 17/320068 606/34 |
| 2008/0058845 | A1* | 3/2008 | Shimizu | A61B 17/29 606/169 |
| 2009/0024161 | A1* | 1/2009 | Bonutti | A61B 17/0401 606/213 |
| 2014/0135663 | A1* | 5/2014 | Funakubo | A61B 17/320068 601/2 |
| 2015/0005771 | A1* | 1/2015 | Voic | A61B 17/14 606/79 |
| 2015/0005774 | A1* | 1/2015 | Voic | A61B 17/320068 606/82 |
| 2015/0005775 | A1* | 1/2015 | Voic | A61B 17/320068 606/83 |
| 2015/0088137 | A1* | 3/2015 | Manna | A61B 17/142 606/79 |
| 2016/0249975 | A1* | 9/2016 | Konishi | A61B 18/1445 606/45 |
| 2017/0086872 | A1* | 3/2017 | Tanigami | A61B 17/3205 |
| 2017/0086874 | A1* | 3/2017 | Tanigami | A61B 17/320068 |
| 2017/0086875 | A1* | 3/2017 | Tanigami | A61B 17/320016 |
| 2017/0156737 | A1* | 6/2017 | Tanigami | A61B 17/320068 |
| 2017/0165507 | A1* | 6/2017 | Tanigami | A61N 7/02 |
| 2018/0185054 | A1* | 7/2018 | Murasawa | A61B 17/16 |
| 2019/0029709 | A1* | 1/2019 | Tanigami | A61B 17/1659 |

OTHER PUBLICATIONS

Jul. 2, 2019 Office Action issued in Japanese Patent Application No. 2018-508301.

Oct. 2, 2018 International Preliminary Report on Patentability issued in International Patent Application No. PCT/JP2016/060780.

* cited by examiner

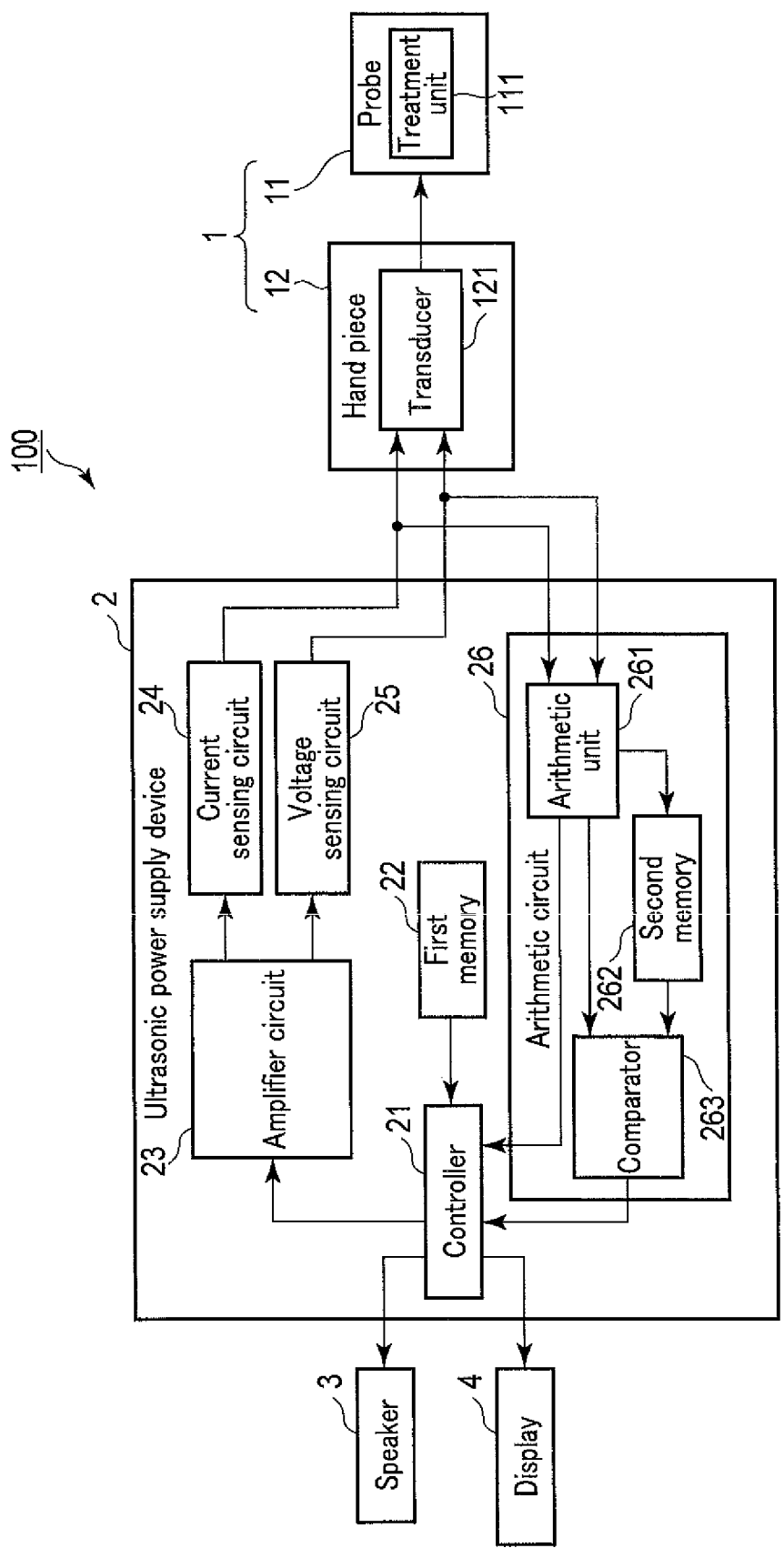
F I G. 1

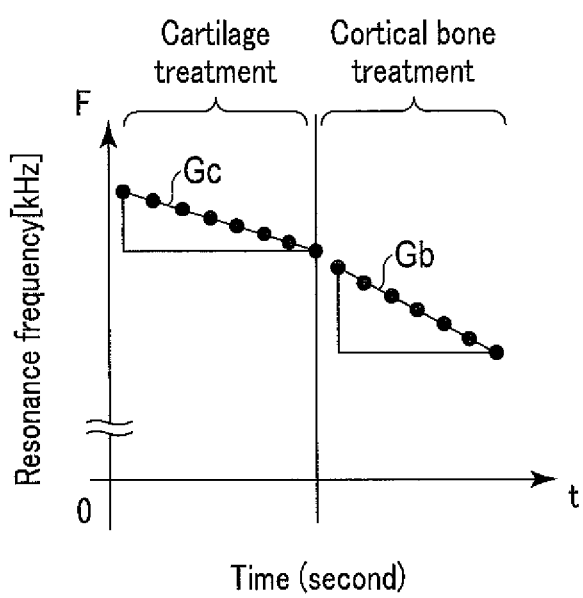
F I G. 4

ULTRASONIC TREATMENT SYSTEM FOR JOINT

CROSS-REFERENCE TO RELATED APPLICATIONS

This application is a Continuation Application of PCT Application No. PCT/JP2016/060780, filed Mar. 31, 2016, the entire contents of which are incorporated herein by reference.

BACKGROUND OF THE INVENTION

1. Field of the Invention

The present invention relates to an ultrasonic treatment system for a joint.

2. Description of the Related Art

In recent years, use of ultrasonic treatment tools for treatment of joints has been discussed. Joints are mainly formed of cartilages and bones formed of cortical bones and cancellous bones. As an ultrasonic treatment tool, for example, a known ultrasonic treatment tool is capable of cutting cartilages and/or bones, as disclosed in Japanese Patent Application Laid-open Publication No. 2003-116870.

In treatment of a joint, the operator aims for cutting only the cartilage in some cases. However, it is difficult to rely on the operator's technique in cutting only the cartilage without cutting the subchondral bone. For this reason, the operator may unintentionally cut the bone (subchondral bone) that does not serve as the treatment target after cutting of the cartilage is finished.

BRIEF SUMMARY OF THE INVENTION

An ultrasonic treatment system for a joint according to an aspect of the present invention comprises: an ultrasonic transducer configured to generate ultrasonic vibration at a predetermined frequency; a treatment unit configured to treat a bone or a cartilage with the ultrasonic vibration; a frequency measurement unit configured to measure the frequency of the ultrasonic vibration of the treatment unit; a calculation unit configured to calculate a tilt indicating change, in a predetermined time, of the frequency measured with the frequency measurement unit; and a controller configured to determine whether change of absolute value of the tilt is equal to or larger than predetermined absolute value of the tilt.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram of an ultrasonic treatment system for a joint according to a first embodiment;

FIG. 4 is a graph of a resonance frequency with respect to the time according to the first embodiment;

DETAILED DESCRIPTION OF THE INVENTION

First Embodiment

Figure 2:
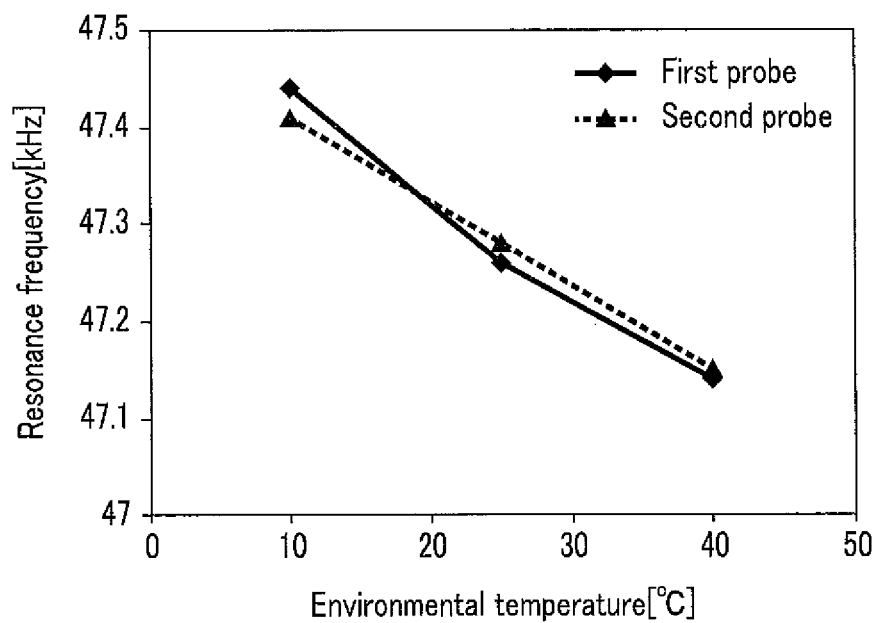
FIG. 2 is a graph of resonance frequencies of probes with respect to environmental temperature according to the first embodiment.

The following is an explanation of an ultrasonic treatment system (hereinafter referred to as "treatment system") for a joint according to a first embodiment to carry out the invention with reference to drawings.

FIG. 1 is a block diagram of a treatment system 100 serving as an example.

The treatment system 100 includes a joint ultrasonic treatment tool (hereinafter referred to as "treatment tool") 1, an ultrasonic power supply device 2, a speaker 3, and a display 4.

The treatment tool 1 includes a probe 11 and a hand piece 12.

The probe 11 transmits ultrasonic vibration. The probe 11 is formed in a rod shape and formed of a material having good vibration transmittance, such as a titanium alloy material. The probe 11 extends in a substantially one direction. The probe 11 includes a treatment unit 111 at a distal end thereof. The treatment unit 111 treats the cartilage and/or bone serving as the treatment target in the joint by ultrasonic vibration. The frequency of ultrasonic vibration of the treatment unit 111 corresponds to the resonance frequency of the probe 11. The frequency of ultrasonic vibration of the treatment unit 111 also corresponds to the frequencies of a current (hereinafter referred to as "output current") and a voltage (hereinafter referred to as "output voltage") output from the ultrasonic power supply device 2 described later to a transducer 121. The treatment unit 111 may be formed in any desired shape suitable for treatment of the cartilage and/or treatment of the bone. The treatment includes melting and cutting.

The following is a brief explanation of differences between cartilages and bones. Cartilages and bones are different in components. Cartilages have a high collagen content, and is known to be molten at, for example, approximately 60° C. to 70° C. By contrast, bones have a high lime content, such as calcium and phosphoric acid, and are harder than cartilages. In addition, bones have a melting point exceeding several hundred degrees centigrade. Cartilages are soft tissues. Bones are hard tissues. The term "bone" used hereinafter indicates at least one of a cortical bone and a cancellous bone. In addition, explanations using cortical bone as an example are also applicable to bones.

The hand piece 12 is configured as a handle for the operator. The hand piece 12 includes a transducer (ultrasonic transducer) 121. The transducer 121 is connected with the probe 11.

The transducer 121 generates ultrasonic vibration at a predetermined frequency, and transmits the ultrasonic vibration to the probe 11.

The ultrasonic power supply device 2 supplies the output current and the output voltage to the transducer 121. The ultrasonic power supply device 2 turning on and off the output current and the output voltage supplied to the transducer 121, to control turning on and off of the operation of the treatment tool 1.

The ultrasonic power supply device 2 includes a controller 21, a first memory 22, an amplifier circuit 23, a current sensing circuit 24, a voltage sensing circuit 25, and an arithmetic circuit 26.

The controller 21 controls each of the units of the ultrasonic power supply device 2. The controller 21 generates the output current and the output voltage serving as references and to be supplied to the transducer 121. The controller 21 supplies the output current and the output voltage serving as references to the amplifier circuit 23.

The first memory (storage unit) 22 stores various types of information. As an example, the first memory 22 stores a threshold A serving as the absolute value of a tilt indicating change of the frequency with a lapse of time in treatment of the bone, as described later.

The amplifier circuit 23 amplifies the output current and the output voltage. The amplifier circuit 23 supplies the output current and the output voltage to the transducer 121.

The current sensing circuit 24 is disposed between the amplifier circuit 23 and the transducer 121. The current sensing circuit 24 senses the value (hereinafter referred to as "output current value") of the output current supplied from the amplifier circuit 23 to the transducer 121. The current sensing circuit 24 transmits the output current value to the arithmetic circuit 26.

The voltage sensing circuit 25 is disposed between the amplifier circuit 23 and the transducer 121. The voltage sensing circuit 25 senses the value (hereinafter referred to as "output voltage value") of the output voltage supplied from the amplifier circuit 23 to the transducer 121. The voltage sensing circuit 25 transmits the output voltage value to the arithmetic circuit 26.

The arithmetic circuit 26 includes an arithmetic unit 261, a second memory 262, and a comparator 263.

The arithmetic unit 261 measures the frequency of ultrasonic vibration of the treatment unit 111. The arithmetic unit 261 also serves as a frequency measurement unit. A measurement example with the arithmetic unit 261 will be described later.

The second memory (storage unit) 262 temporarily stores the value of the frequency measured with the arithmetic unit 261.

The comparator 263 calculates a tilt indicating change of the frequency of ultrasonic vibration of the treatment unit 111 measured with the arithmetic unit 261 for a predetermined time. The comparator 263 also serves as a calculator. A calculation example with the comparator 263 will be described later.

The speaker 3 outputs a warning message by sound on the basis of a notification instruction from the controller 21.

The display 4 displays a warning message on the screen on the basis of the notification instruction from the controller 21.

The following is an explanation of regulation of the frequencies of the output current and the output voltage with the controller 21.

The controller 21 receives the output current value and the output voltage value from the arithmetic unit 261. The controller 21 detects impedance on the basis of the output voltage value, the output current value, and a phase difference between the output voltage and the output current. The impedance is a value obtained by adding the impedance of the treatment tool 1 itself to the impedance caused by the tissue that the treatment unit 111 contacts. The controller 21 senses the resonance frequency of the probe 11, with reference to the output voltage value, the output current value, and the impedance. The controller 21 regulates the frequencies of the output current and the output voltage such that the sensed resonance frequency is set as the frequencies of the output current and the output voltage.

The following is an explanation of a tilt Gb indicating change of the resonance frequency with a lapse of time in treatment of the cortical bone.

As explained hereinafter, the tilt Gb can be acquired from the graph illustrated in FIG. 4 that can be acquired from the graph illustrated in FIG. 2 and the graph illustrated in FIG. 3.

FIG. 2 is a graph of the resonance frequencies of probes for the environmental temperature, serving as an example. FIG. 2 illustrates a graph of each of a desired first probe and a second probe. FIG. 2 illustrates that the resonance frequency of the probe 11 substantially linearly decreases as the environment temperature increases. In this example, the resonance frequency of the probe is F [kHz], and the environmental temperature is T1 [° C.]. In view of above, F [kHz] can be expressed as "F=f (T1)", as the function of T1 [° C.].

Figure 3:
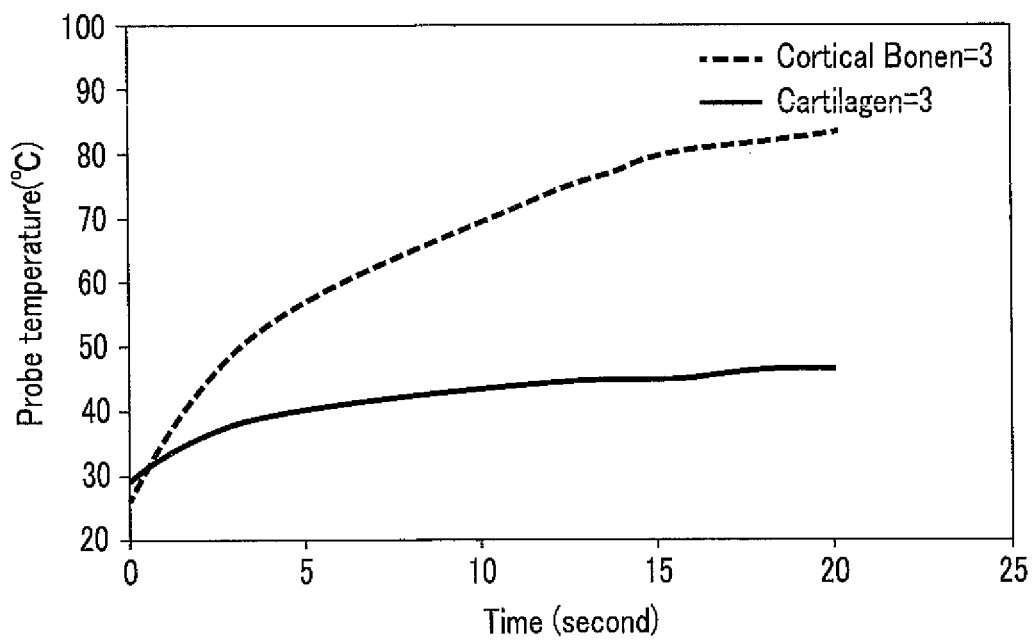
FIG. 3 is a graph of a probe temperature with respect to the time according to the first embodiment.

FIG. 3 is a graph of the probe temperature with respect to the time, serving as an example. FIG. 3 illustrates the average of a plurality of measurement results (the temperature of the probe 11 with respect to the time) for each of the cartilage and the cortical bone. The symbol n in FIG. 3 indicates the number of measurements. FIG. 3 illustrates that the probe temperature increases with a lapse of time in each of the cases of the cartilage and the cortical bone. FIG. 3 also illustrates that the cartilage and the cortical bone are different in change (increase rate) of the probe temperature per predetermined time. Specifically, FIG. 3 illustrates that the increase rate of the probe temperature in treatment of the cortical bone is larger than the increase rate of the probe temperature in treatment of the cartilage. In this example, the probe temperature is T2 [° C.], and the time it t [seconds]. Based on above, T2 [° C.] can be expressed as "T2=g (t)", as the function of t [seconds].

FIG. 4 is a graph of the resonance frequency with respect to the time when treatment is performed on the cartilage.

The graph illustrated in FIG. 4 can be acquired by correlating the environmental temperature of the graph illustrated in FIG. 2 with the probe temperature of the graph illustrated in FIG. 3. By correlating T2 in the function "T2=g (t)" in FIG. 3 with T1 in the function "F=f (T1)" in FIG. 2, the function "F=f (g (t))" is acquired as the function of the resonance frequency [kHz] of the probe with respect to the time [seconds]. FIG. 4 illustrates that the resonance frequency in treatment of the cortical bone is lower than the resonance frequency in treatment of the cartilage. In addition, the change of the resonance frequency with a lapse of time in treatment of the cortical bone and the change of the resonance frequency with a lapse of time in treatment of the cartilage can be regarded as a straight line at each temperature by differentiating FIG. 3. FIG. 4 illustrates that the absolute value of the tilt Gb indicating change of the resonance frequency with a lapse of time in treatment of the cortical bone is larger than the absolute value of the tilt Gc indicating change of the resonance frequency with a lapse of time in treatment of the cartilage.

The following is an explanation of the waveform of the output voltage sensed with the voltage sensing circuit 25.

Figure 5:
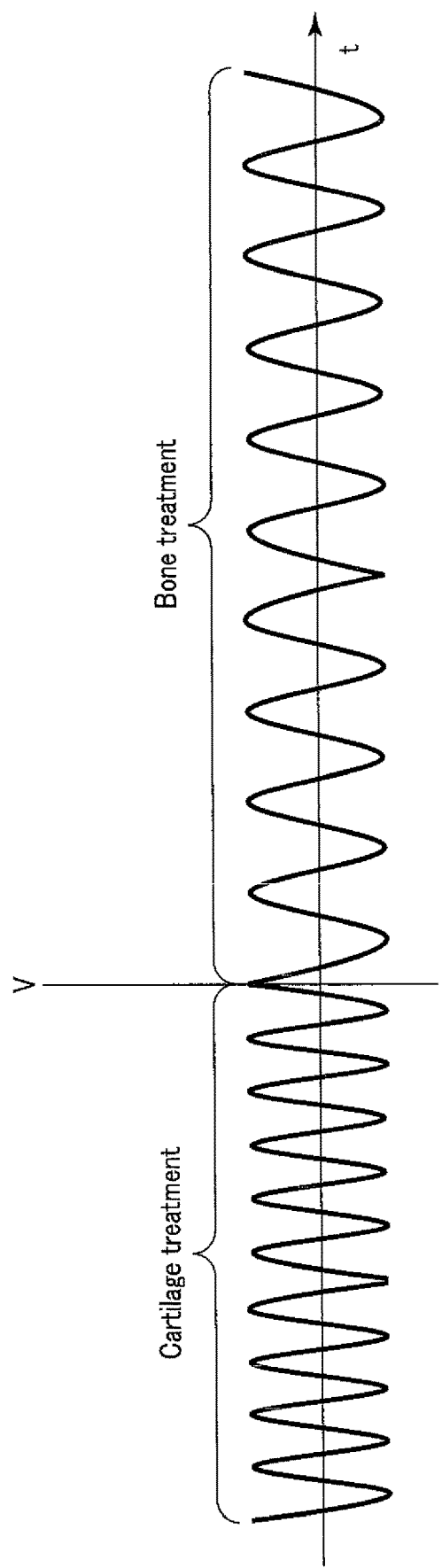
FIG. 5 is a graph of an output voltage with respect to the time according to the first embodiment.

FIG. 5 is a graph of the output voltage with respect to the time, serving as an example. The output voltage is a sine wave. As described above, the frequency of the output voltage is regulated to the resonance frequency of the probe 11 with the controller 21. For this reason, the frequency of the output voltage in treatment of the bone is lower than the frequency of the frequency of the output voltage in treatment of the cartilage (see FIG. 4). The waveform of the output current sensed with the current sensing circuit 24 is similar to the waveform of the output current illustrated in FIG. 5.

The following is an explanation of detection of the tissue being treated on the basis of the frequency of the output voltage.

Figure 6:
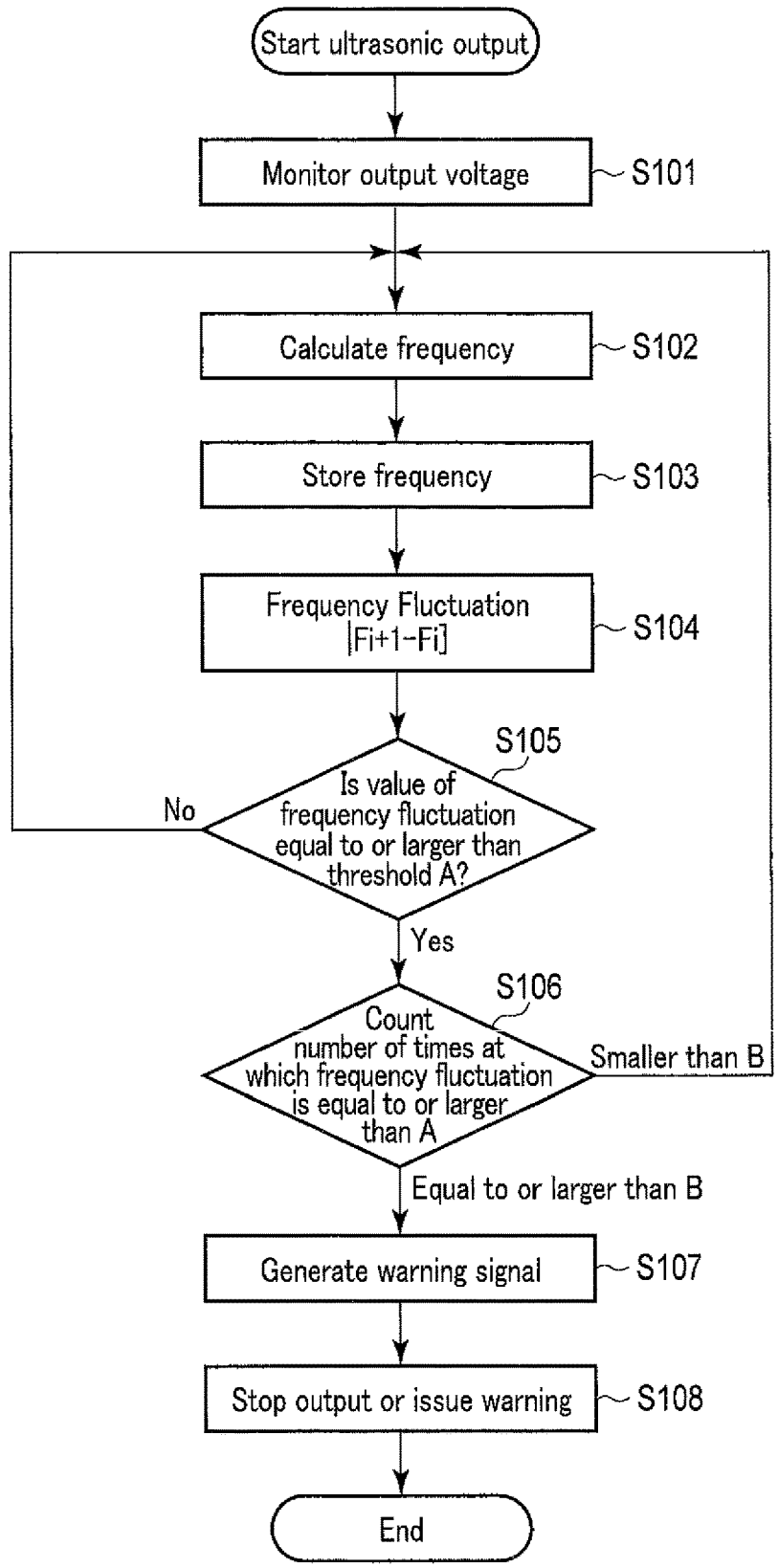
FIG. 6 is a flowchart illustrating a process to detect the tissue being treated according to the first embodiment.

FIG. 6 is a flowchart illustrating a process for detecting the tissue being treated, serving as an example.

Figure 7:
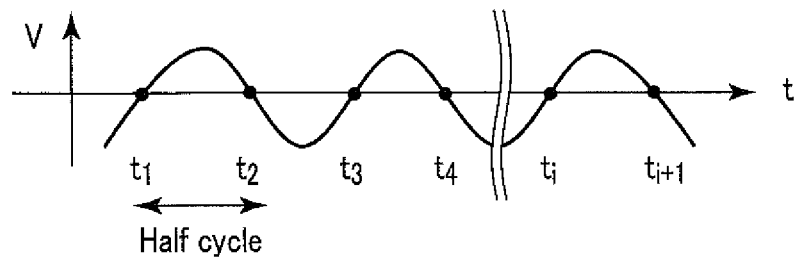
FIG. 7 is a graph of the output voltage with respect to the time according to the first embodiment.

The arithmetic unit 261 monitors the output voltage sensed with the voltage sensing circuit 25 (Step S101). At Step S101, the arithmetic unit 261 acquires points of time $t_1$, $t_2$, . . . , and $t_N$, at which the output voltage is zero, using a field programmable gate array (FPGA), as illustrated in FIG. 7.

The arithmetic unit 261 calculates the frequency of the output voltage (Step S102). At Step S102, the arithmetic unit 261 calculates the frequency of the output voltage on the basis of $F_i=\frac{1}{2}(t_{i+1}-t_i)$. The symbol i is 1, 2, . . . , and N. As described above, because the frequency of the output voltage corresponds to the frequency of the ultrasonic vibration of the treatment unit 111, it can also be said that the arithmetic unit 261 calculates the frequency of the ultrasonic vibration of the treatment unit 111.

The arithmetic unit 261 stores the value of the frequency $F_i$ of the output voltage calculated at Step S102 in the second memory 262 (Step S103). The arithmetic unit 261 also transmits the value of the frequency $F_i$ of the output voltage calculated at Step S102 to the comparator 263.

The comparator 263 calculates the frequency fluctuation $|F_{i+1}-F_i|$ using the frequency $F_{i+1}$ calculated with the arithmetic unit 261 and the frequency $F_i$ stored in the second memory 262 (Step S104). The change (frequency fluctuation) of the frequency of the ultrasonic vibration of the treatment unit 111 calculated with the comparator 263 corresponds to a tilt indicating change in the frequency of the ultrasonic vibration of the treatment unit 111. The comparator 263 transmits the value of the frequency fluctuation to the controller 21.

The controller 21 determines whether change of the absolute value of the tilt indicating change in frequency of the ultrasonic vibration of the treatment unit 111 is equal to or larger than the predetermined absolute value of the tilt (Step S105). At Step S105, the controller 21 compares the frequency fluctuation corresponding to the absolute value of the tilt indicating change in frequency of the ultrasonic vibration of the treatment unit 111 with a threshold A, and determines whether the value of the frequency fluctuation is equal to or larger than the threshold A (Step S105). The threshold A is set within a range of, for example, 0.07 to 0.13 [kHz/s]. The value "0.07" in the threshold A is the smallest absolute value of the tilt in the range that the tilt in cutting of the cartilage can take, and the value "0.13" is the largest absolute value of the tilt in the range that the tilt in cutting of the bone can take. Specifically, in the case of the tilt with the absolute value larger than 0.07, it can be considered that the treatment unit 111 is out of cutting of the cartilage, and it can be considered that the treatment unit 111 is surely cutting the bone at the time when the absolute value of the tilt becomes larger than 0.13. For this reason, by setting the threshold to the values between 0.07 and 0.13, the threshold can be considered to be a valid value based on which it is considered that cutting of the cartilage is finished and cutting of the bone has started. The reason why the range that the tilt can take occurs in cutting of the cartilage and the bone is that the range is generated, for example, due to the difference in value according to the type of the probe in the graph of FIG. 2, or when the increase rate of the probe temperature of FIG. 3 is calculated, in calculation of the graph (function) illustrated in FIG. 4. The values of this range are values in the case where the fixed pressing force is fixed to 3N. The threshold may be changed according to change of the pressing force. When the value of the frequency fluctuation is equal to or larger than the threshold A, the treatment unit 111 can be regarded as treating the bone. When the value of the frequency fluctuation is smaller than the threshold A, the treatment unit 111 can be regarded as treating the cartilage.

When the value of the frequency fluctuation is not equal to or larger than the threshold A (No at Step S105), the process proceeds from Step S105 to Step S102. When the value of the frequency fluctuation is equal to or larger than the threshold A (Yes at Step S105), the controller 21 counts the number of times at which the value of the frequency fluctuation is equal to or larger than the threshold A (Step S106). At Step S106, the controller 21 determines whether the number of times at which the value of the frequency fluctuation is equal to or larger than the threshold A is equal to or larger than the number B. B is an integer of 1 or more. When B is set to 2 or more, the controller 21 performs the processing of Step S105 described above at least twice. This structure improves the accuracy of determination of the tissue being treated with the treatment unit 111.

When the number of times at which the value of the frequency fluctuation is equal to or larger than the threshold A is smaller than the number B, the process proceeds from Step S106 to Step S102.

When the number of times at which the value of the frequency fluctuation is equal to or larger than the threshold A is equal to or larger than the number B, the controller 21 generates a warning signal (Step S107). At Step S107, the controller 21 outputs, as the warning signal, at least one of an instruction to stop the ultrasonic vibration generated with the transducer 121 and a notification instruction.

The ultrasonic power supply device 2 performs processing in accordance with the details of the warning signal generated with the controller 21 (Step S108). As an example, the amplifier circuit 23 stops supply of the output current and the output voltage to the transducer 121 on the basis of stop instruction from the controller 21. The amplifier circuit 23 may decrease the output current and the output voltage, instead of stopping supply of the output current and the output voltage to the transducer 121. As another example, the speaker 3 outputs a warning message by sound on the basis of the notification instruction from the controller 21. The warning message may be any message notifying the operator that the treatment unit 111 has reached the bone. In the same manner, the display 4 outputs a warning message on the screen on the basis of the notification instruction from the controller 21.

According to the first embodiment, the ultrasonic treatment system 100 for a joint is enabled to detect which of the cartilage and the bone is being treated. This structure enables the ultrasonic treatment system 100 for a joint to suppress the operator's unintentional advance of cutting of the bone after cutting of the cartilage is finished to the minimum, in treatment of a joint with the purpose of cutting only the cartilage.

The following is an explanation of some modifications of the first embodiment.

The following is an explanation of a first modification. The treatment system 100 may detect the tissue being treated on the basis of the frequency of the output current, instead of the frequency of the output voltage. At Step S101 described above, the arithmetic unit 261 monitors the output current sensed with the current sensing circuit 24. At Step S102, the arithmetic unit 261 calculates the frequency of the output current, in the same manner as calculation of the frequency of the output voltage.

The following is an explanation of a second modification. The treatment system 100 may detect the tissue being treated on the basis of the frequency of the output power, instead of the frequency of the output voltage. At Step S101 described above, the arithmetic unit 261 monitors the output power serving as the product of the output current sensed with the current sensing circuit 24 multiplied by the output voltage sensed with the voltage sensing circuit 25. At Step S102 described above, the arithmetic unit 261 calculates the frequency of the output power, in the same manner as calculation of the frequency of the output voltage.

The following is an explanation of a third modification. The first memory 22 may store data of a threshold B serving as the absolute value of the tilt indicating change of the resonance frequency with a lapse of time in treatment of the cartilage, in addition to the data of the threshold A. In this example, at Step S105 described above, the controller 21 determines which of the threshold A and the threshold B the frequency fluctuation is close to. When the frequency fluctuation is close to the threshold A, the treatment unit 111 can be regarded as treating the bone. When the frequency fluctuation is close to the threshold A, the controller 21 counts, at Step S106 described above, the number of times at which it is determined that the frequency fluctuation is close to the threshold A. When the frequency fluctuation is close to the threshold B, the treatment unit 111 can be regarded as treating the cartilage. When the frequency fluctuation is close to the threshold B, the process proceeds from Step S105 to Step S102 described above.

The third modification enables the ultrasonic treatment system 100 for a joint to detect, with high accuracy, which of the cartilage and the bone is being treated, regardless of the pressing force.

The following is an explanation of a fourth modification. At Step S105 described above, the controller 21 may determines whether the frequency fluctuation is rapid. At Step S105, for example, the controller 21 determines whether change of the absolute value of the tilt indicating change of the frequency of the ultrasonic vibration of the treatment unit 111 is equal to or larger than the predetermined absolute value of the tilt. The predetermined absolute value of the tilt is a value obtained by increasing the absolute value of the tilt indicating change of the frequency of the ultrasonic vibration of the treatment unit 111 by 30%. When the frequency fluctuation is not rapid, the process proceeds from Step S105 to Step S102 described above. When the frequency fluctuation is rapid, the controller 21 omits Step S106 described above, and performs processing of Step S107 described above. In this example, the first memory 22 may store no data of the threshold A.

The fourth modification enables the ultrasonic treatment system 100 for a joint to detect, with high accuracy, which of the cartilage and the bone is being treated, regardless of the pressing force.

Second Embodiment

The following is an explanation of the second embodiment. The following description hereinafter mainly illustrates a part different from the first embodiment.

The second embodiment illustrates a mode of detecting which of the cartilage and the bone is being treated, in accordance with the frequency of the output voltage.

The treatment system 100 according to the second embodiment may exclude the second memory 262 and the comparator 263 in the arithmetic circuit 26 in FIG. 1. In this example, the treatment system 100 detects the tissue using a difference in frequency between the cartilage treatment and the bone treatment illustrated in FIG. 4 and FIG. 5. As described above, the frequency of the output voltage in treatment of the bone is lower than the frequency of the output voltage in treatment of the cartilage. The first memory 22 stores data of the threshold (x value) of the frequency, instead of the data of the threshold A.

The following is an explanation of detection of the tissue being treated on the basis of the frequency of the output voltage.

Figure 8:
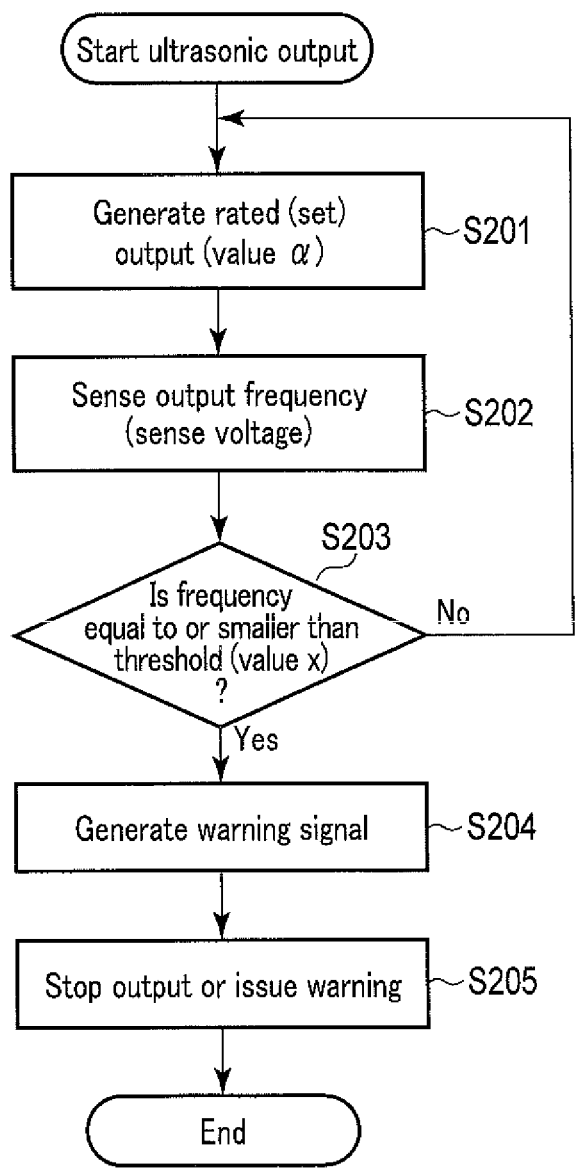
FIG. 8 is a flowchart for detection of the tissue being treated according to a second embodiment.

FIG. 8 is a flowchart illustrating a process for detecting the tissue being treated, serving as an example.

The controller 21 generates a rated (set) output (value α) (Step S201). The value α corresponds to the output current and the output voltage serving as the reference and explained in the first embodiment.

The arithmetic unit 261 senses the frequency of the output voltage (Step S202). At Step S202, the arithmetic unit 261 calculates the frequency of the output voltage on the basis of the output voltage sensed with the voltage sensing circuit 25, in the same manner as Step S102 described above. The arithmetic unit 261 transmits the value of the frequency of the output voltage to the controller 21.

The controller 21 determines whether the value of the frequency of the output voltage is equal to or smaller than the threshold (value x) stored in the first memory 22 (Step S203). When the value of the frequency of the output voltage is not equal to or smaller than the threshold (value x), the treatment unit 111 can be regarded as treating the cartilage. When the value of the frequency of the output voltage is equal to or smaller than the threshold (value x), the treatment unit 111 can be regarded as treating the bone.

When the value of the frequency of the output voltage is not equal to or smaller than the threshold (value x) (No at Step S203), the process proceeds from Step S203 to Step S201.

When the value of the frequency of the output voltage is equal to or smaller than the threshold (value x) (Yes at Step S203), the controller 21 generates a warning signal (Step S204), in the same manner as Step S107 described above. Thereafter, in the same manner as Step S108 described above, the ultrasonic power supply device 2 performs processing in accordance with the details of the warning signal generated with the controller 21 (Step S205).

The second embodiment enables the ultrasonic treatment system 100 for a joint to acquire effects similar to the effects explained in the first embodiment.

The following is an explanation of a modification of the second embodiment. The treatment system 100 may detect the tissue being treated on the basis of the frequency of the output current or the frequency of the output power, instead of the frequency of the output voltage. In this case, at Step S202 described above, it suffices that the arithmetic unit 261 calculates the frequency of the output current or the frequency of the output power, as explained in the first embodiment.

Some embodiments have been specifically described above with reference to the drawings, but the present invention is not limited to the embodiments described above. The present invention includes all modes carried out within a range not departing from the gist of the invention.

What is claimed is:

1. An ultrasonic treatment system for a joint, comprising:
    an ultrasonic treatment tool configured to treat a cartilage located in a position surrounding a bone forming a joint; and
    a power supply device configured to supply energy driving the ultrasonic treatment tool, wherein
    the ultrasonic treatment tool includes:
    a treatment unit configured to generate ultrasonic vibration with the supplied energy, cut the cartilage with a temperature increasing at a first temperature increase rate by frictional heat, and cut the bone with a temperature increasing at a second temperature increase rate higher than the first temperature increase rate, and
    the power supply device includes:
    a storage unit configured to store a first value corresponding to a first tilt indicating change, in a predetermined time, of a frequency of the ultrasonic vibration and corresponding to the first temperature increase rate;
    an arithmetic unit configured to acquire the frequency of the ultrasonic vibration of the ultrasonic treatment tool;
    a calculation unit configured to calculate a second value corresponding to a second tilt indicating change, in a predetermined time, of the acquired frequency; and
    a controller configured to repeat acquisition of the frequency of the ultrasonic vibration with the arithmetic unit and calculation of the second value with the calculation unit, when the second value is smaller than the first value, the controller counting the number of times at which the second value is equal to or larger than the first value, when the second value is equal to or larger than the first value, and performing different processes in accordance with a count value.

2. The ultrasonic treatment system according to claim 1, wherein the storage unit further stores a second value corresponding to a second tilt indicating change, at a predetermined time, of the frequency of the ultrasonic vibration and corresponding to the second temperature increase rate, and
    the controller outputs at least one of an instruction to stop the ultrasonic vibration and a notification instruction, when the value is close to the second value from the first value.

3. The ultrasonic treatment system according to claim 1, wherein
    the first value is a value set within a range of 0.07 to 0.13 kHz/s.

4. The ultrasonic treatment system according to claim 1, wherein the arithmetic unit is formed of a field programmable gate array (FPGA).

5. A power supply device supplying energy driving an ultrasonic tool treating a cartilage located in a position surrounding a bone forming a joint, comprising:
    a storage unit configured to store a first value corresponding to a first tilt indicating change, in a predetermined time, of a frequency of ultrasonic vibration of the ultrasonic treatment tool and corresponding to a first temperature increase rate;
    an arithmetic unit configured to acquire the frequency of the ultrasonic vibration driving the ultrasonic treatment tool;
    a calculation unit configured to calculate a second value corresponding to a second tilt indicating change, in a predetermined time, of the acquired frequency of the ultrasonic vibration; and
    a controller configured to repeat acquisition of the frequency of the ultrasonic vibration with the arithmetic unit and calculation of the second value with the calculation unit, when the second value is smaller than the first value, the controller counting the number of times at which the second value is equal to or larger than the first value, when the second value is equal to or larger than the first value, and performing different processes in accordance with a count value.

6. An ultrasonic treatment method for a joint performed with an ultrasonic treatment system for a joint including an ultrasonic treatment tool configured to treat a cartilage located in a position surrounding a bone forming a joint, and a power supply device configured to supply energy driving the ultrasonic treatment tool, the method comprising:
    generating ultrasonic vibration with the supplied energy, cutting the cartilage with a temperature increasing at a first temperature increase rate by frictional heat, and cutting the bone with a temperature increasing at a second temperature increase rate higher than the first temperature increase rate, with the ultrasonic treatment tool;
    acquiring a frequency of the ultrasonic vibration of the ultrasonic treatment tool, with the power supply device storing a first value corresponding to a first tilt indicating change, in a predetermined time, of a frequency of the ultrasonic vibration and corresponding to the first temperature increase rate,
    calculating a second value corresponding to a second tilt indicating change, in a predetermined time, of the acquired frequency, with the power supply device,
    repeating acquisition of the frequency of the ultrasonic vibration of the ultrasonic treatment tool and calculation of the second value, when the second value is smaller than the first value, with the power supply device, and counting the number of times at which the second value is equal to or larger than the first value, when the second value is equal to or larger than the first value, and performing different processes in accordance with a count value, with the power supply device.

* * * * *